United States Patent
Tiwald et al.

(10) Patent No.: US 9,599,569 B2
(45) Date of Patent: Mar. 21, 2017

(54) METHOD TO ENHANCE SENSITIVITY TO SURFACE NORMAL OPTICAL FUNCTIONS OF ANISOTROPIC FILMS USING ATTENUATED TOTAL REFLECTION

(71) Applicant: J.A. WOOLLAM CO., INC., Lincilen, NE (US)

(72) Inventors: Thomas E. Tiwald, Lincoln, NE (US); Jeremy A. Van Derslice, Lincoln, NE (US)

(73) Assignee: J.A. WOOLLAM CO., INC., Lincoln, NE (US)

(*) Notice: Subject to any disclaimer, the term of this patent is extended or adjusted under 35 U.S.C. 154(b) by 0 days.

(21) Appl. No.: 14/999,365

(22) Filed: Apr. 28, 2016

(65) Prior Publication Data

US 2016/0274032 A1  Sep. 22, 2016

Related U.S. Application Data

(63) Continuation-in-part of application No. 14/120,482, filed on May 22, 2014, now abandoned.

(60) Provisional application No. 61/855,944, filed on May 28, 2013.

(51) Int. Cl.

| | | |
|---|---|---|
| C23C 16/52 | (2006.01) |
| C23C 14/28 | (2006.01) |
| H05B 6/00 | (2006.01) |
| G01N 21/84 | (2006.01) |
| G02B 5/30 | (2006.01) |
| G02B 1/11 | (2015.01) |
| G02B 5/04 | (2006.01) |
| G02B 5/06 | (2006.01) |
| G01M 11/00 | (2006.01) |
| G01N 21/552 | (2014.01) |

(52) U.S. Cl.
CPC ......... *G01N 21/8422* (2013.01); *G01M 11/00* (2013.01); *G01N 21/552* (2013.01); *G02B 1/11* (2013.01); *G02B 5/04* (2013.01); *G02B 5/06* (2013.01); *G02B 5/3083* (2013.01)

(58) Field of Classification Search
CPC ........................... G01N 21/211; G01N 21/552
USPC ....................................... 427/8, 595
See application file for complete search history.

(56) References Cited

U.S. PATENT DOCUMENTS

| | | | |
|---|---|---|---|
| 5,437,840 A | 8/1995 | King et al. | 422/82.08 |
| 5,633,724 A | 5/1997 | King et al. | 356/445 |
| 6,738,139 B1 | 5/2004 | Synowicki et al. | |
| 7,187,443 B1 | 3/2007 | Synowicki et al. | |
| 7,239,391 B2 | 7/2007 | Synowicki et al. | |
| 7,265,839 B1 | 9/2007 | Tiwald | |
| 7,636,161 B1 | 12/2009 | Tiwald | |
| 7,777,883 B2 | 8/2010 | Synowicki et al. | |
| 7,817,266 B2 * | 10/2010 | Pfeiffer | G01N 21/00 356/246 |
| 7,920,264 B1 | 4/2011 | Tiwald | |
| 8,130,375 B1 | 3/2012 | Pfeiffer et al. | |
| 8,531,665 B1 | 9/2013 | Pfeiffer et al. | |
| 2008/0130004 A1 | 6/2008 | Pyo et al. | 356/445 |
| 2010/0167946 A1 | 7/2010 | Shaw et al. | 506/9 |
| 2013/0114079 A1 | 5/2013 | Zheng et al. | 356/364 |

(Continued)

*Primary Examiner* — Kelly M Gambetta
(74) *Attorney, Agent, or Firm* — James D. Welch

(57) ABSTRACT

Methodology for determining optical functions of thin films with enhanced sensitivity to "p" polarized electromagnetic radiation reflected from both interfaces of an absorbing film.

30 Claims, 7 Drawing Sheets

(56) References Cited

U.S. PATENT DOCUMENTS

2013/0293896 A1* 11/2013 Fujimaki .............. G01N 21/553
356/445
2014/0170024 A1 6/2014 Fujimaki et al. ............... 422/69

* cited by examiner

Note: $\theta_C$ can be any angle where $\sin \theta_C \geq n_{air} / n_{prism}$ Incident beam does NOT need to enter prism normal to entrance face $\theta_C$ can be any angle where $\sin \theta_C \geq n_{air} / n_{prism}$

METHOD TO ENHANCE SENSITIVITY TO SURFACE NORMAL OPTICAL FUNCTIONS OF ANISOTROPIC FILMS USING ATTENUATED TOTAL REFLECTION

This application is a CIP of application Ser. No. 14/120,482 Filed May 22, 2014, and therevia Claims benefit of Provisional Application Ser. No. 61/855,944 filed May 28, 2013.

TECHNICAL FIELD

The present invention relates to methods for determining optical functions of thin films, and more particularly to methodology for enhancing the sensitivity to "p" polarized electromagnetic radiation reflected from both interfaces of an anisotropic absorbing film.

BACKGROUND

It is well known to investigate thin films with electromagnetic radiation. For instance over 170 Patents by the J.A. Woollam company provide great insight to many aspects of the technique. Some of the more relevant thereof as regards the present invention are:
  U.S. Pat. Nos. 7,265,839 and 7,920,264 to Tiwald, which discloses a Horizonataly Oriented Attenuation total Reflection system for application in methodology that apply Spectroscopic Ellipsometer or Polarimeter systems;
  U.S. Pat. No. 7,636,161 to Tiwald which discloses a system and method for reducing reflections of a beam of electromagnetism from the back surface of a sample;
  U.S. Pat. No. 6,738,139 to Synowicki et al., which discloses a method for determining bulk refractive indicies of fluids utilizing thin films thereof on a roughened surface of a two sided rigid or semirigid object;
  U.S. Pat. No. 7,777,883 to Synowicki et al., which discloses a system for reducing reflections of a beam of electromagnetic radiation from the back surface of an anisotropic sample, and methodology of for investigating the incident front surface thereof with electromagnetic radiation;
  U.S. Pat. No. 7,187,443 to Synowicki et al., which discloses a method for determining bulk refractive indicies of flowable liquids utilizing thin films thereof on a roughened surface of a rigid or semirigid object;
  U.S. Pat. No. 7,239,391 to Synowicki et al., which discloses Spectroscopic ellipsometer system mediated methodology for quantifying later defining parameters in mathematical models of samples which contain a plurality of layers of different materials, at least some of which are absorbing of electromagnetic radiation;
  U.S. Pat. Nos. 8,531,665, 8,130,375 and 7,817,266 to Pfeiffer et al. which describe small internal volume cells having fluid entry and exit ports for use in ellipsometer systems that cause electromagnetic radiation to reflect from samples therewithin.
  Published Patent Applications to Fujimaki et al. Nos. 2013/0293896 and 2014/0170024 describe systems for investigating refractive index changing materials comprising use of Surface Plasmon Resonance (SPR) and Waveguide effects, preferably using an "S" polarized beam of electromagnetic radiation. A Detection Plate that is constructed from a Glass Substrate upon which is caused to be present Silicon and Silicon Oxide layers, is positioned so as to receive materials on the Silicon Oxide layer, and the presence of such materials changes the refractive index, leading to changes in Reflectivity, which can be measured. Electromagnetic radiation is directed to interact with the Detection Plate and materials present at it's Silicon Oxide layer via an optical Prism that imposes a Total Internal Reflection configuration at the point whereat the Silicon Oxide and Index changing materials are caused to be present. These references concern improving results obtainable by application of Surface Plasmon Resonance effects, by combining them with the effects of Waveguides. These references are focused on investigation of isotropic materials and make no reference to enhancing detection of surface-normal optical reflections from anisotropic thin films using attenuated total internal reflection. Doing so, as does the present invention, greatly enhances the ability to detect even very small, (eg. when 1% of that parallel to a sample surface plane, is present perpendicular to said sample surface plane), anisotropic properties in a sample, so that a majority of a "p" polarized beam of electromagnetic radiation interacting with said anisotropic absorbing sample appears in a measurable "rp" coefficient, where "rp" is a Freshnel Coefficient in the basic equation of Ellipsometry:

$$p = r_p/r_s \, \mathrm{Tan}(\psi) \exp(i\Delta).$$

Note "rs" refers to that component of a polarized beam of electromagnetic radiation which is parallel to said sample surface plane, while "rp" is perpendicular thereto, and Psi ($\psi$) and Delta ($\Delta$) are a ratio of "rp" and "rs", and phase angle therebetween, respectively.

It is emphasized that the two Fujimaki et al. 896 and 024 references do not concern or suggest measurement of anisotropic surface-normal sample properties, let alone enhancement thereof. The thin film in said 896 and 024 references is not a material that is deposited onto a substrate which demonstrate anisotropic effects, but rather the system thereof detects changes in reflectivity caused in said system based on material added later which is caused to adhere to a surface in said system. As is presented later in this Specification, the present invention is focused on measuring anisotropic effects in absorbing samples which are deposited onto a substrate, with greater sensitivity than is possible when doing direct investigation thereof with electromagnetic radiation. Further, no added materials are involved that serve to change reflectivity in the present invention system.
  Additional known references are:
  U.S. Pat. Nos. 5,633,724 and 5,437,840; and
Published Applications:
  2010/0167946 by Shaw et al.; 2013/0114079 by Zheng et al. and 2008/0130004 by Pyo et al.
  The references cited are incorporated by reference hereinto.

Even in view of known prior art, need remains for methodology that enables determining surface normal optical functions of anisotropic absorbing thin films, and more particularly to methodology for enhancing the sensitivity to "p" polarized electromagnetic radiation reflected from both interfaces of an anisotropic absorbing film.

DISCLOSURE OF THE INVENTION

The present invention is method to enhance sensitivity to surface-normal optical functions of anisotropic films using attenuated total reflection (ATR). It comprising the steps of: in either order, steps a) and b):
  a) providing a transparent prism having three sides, a first and second of which are offset from one another by an apex angle which is sufficient to cause total reflection of an electromagnetic beam entered into the first side of the transparent prism, at the third side of the transparent prism when the ambient is air;

b) providing a transparent substrate having first and second substantially parallel sides separated by a substrate thickness;

c) depositing an anisotropic absorbing thin film on one side of said substrate, said anisotropic absorbing thin film having two sides;

d) forming a system by positioning said third side of said prism which is opposite the apex angle in contact with the side of the substrate opposite that onto which was deposited the anisotropic absorbing thin film.

Said method continues with:

e) causing an incident beam of electromagnetic radiation to enter the first of said two sides of said transparent prism that are offset from one another by said apex angle along a locus such that said beam passes through said transparent prism and transparent substrate, totally internally reflects from both sides of said anisotropic absorbing thin film, passes back through said transparent substrate and transparent prism and exists the second side thereof;

f) applying a detector of said electromagnetic radiation placed at a position such that said beam of electromagnetic radiation that exists said second side of said prism enters thereinto;

g) analyzing data produced by said detector to determine surface-normal optical properties of said anisotropic absorbing thin film with increased sensitivity, as compared to results achievable by direct investigation thereof.

Said method is characterized in that no waveguide effects are required for it to achieve its results, and in that no materials are added to the system formed in steps a)-d) during practice thereof that serve to change reflectivity in said system.

Said method can involve using refractive index matching material being placed at the point of contact between said transparent substrate and said transparent prism to minimize reflections from said point of contact therebetween, and said material can be a fluid.

Said method can involve the transparent prism and transparent substrate being merged into a single element and the anisotropic absorbing thin film is deposited onto the third side of the transparent prism that is opposite the apex degree angle.

Said method can provide that the transparent prism having three sides, a first and second of which are offset from one another by said apex is modified such that the apex angle is cut away therefrom thereby providing a fourth side which is typically, but not necessarily, substantially parallel to said side of said transparent prism which was opposite said cut away apex angle which is positioned on the side of said transparent substrate opposite to that upon which was deposited a anisotropic absorbing thin film.

Said method can involve the transparent prism being modified by removal of said apex angle to provide said fourth side, is hollow and inside of which there is caused to be present a fluid.

Said method can involve the electromagnetic beam being polarized to comprise a "p" component, and it is the selectively the "p" component that is analyzed in step g.

Said method can further comprise:

h) providing a substrate;

i) depositing an anisotropic absorbing thin film on said substrate which is functionally the same as that in step c);

j) causing an incident beam of electromagnetic radiation to reflect from said anisotropic absorbing thin film;

k) applying a detector of said electromagnetic radiation placed at a position such that said beam of electromagnetic radiation that reflects from said anisotropic absorbing thin film enters thereinto;

l) analyzing data produced by said detector to determine optical properties of said anisotropic absorbing thin film; and m) comparing said analyzed data in step l) to that obtained in step e) and evaluating the enhanced sensitivity to surface normal optical functions of anisotropic films achieved by using attenuated total reflection achieved in step g.

Another method to enhance sensitivity to surface-normal optical functions of anisotropic films using attenuated total reflection comprises the steps of:

a) providing a transparent prism having three sides, a first and second of which are offset from one another by an apex angle which is sufficient to cause total reflection of an electromagnetic beam entered into the first side of the transparent prism, at the third side of the transparent prism when the ambient is air;

b) forming a system by depositing an anisotropic absorbing thin film on the third side of said prism which is opposite said apex angle, said anisotropic absorbing thin film having two sides;

c) causing an incident beam of electromagnetic radiation to enter the first of said two sides of said transparent prism that are offset from one another by said apex angle, along a locus such that said beam passes through said transparent prism, totally internally reflects from both sides of said anisotropic absorbing thin film, passes back through said transparent prism and exists the second side thereof.

Said method continues with:

d) applying a detector of said electromagnetic radiation placed at a position such that said beam of electromagnetic radiation that exists said second side of said prism enters thereinto;

e) analyzing data produced by said detector to determine surface-normal optical properties of said anisotropic absorbing thin film with increased sensitivity, as compared to results achievable by direct investigation thereof.

Said method is characterized in that no waveguide effects are required for it to achieve its results, and in that no materials are added to the system formed in steps a)-b) during practice thereof that serve to change reflectivity in said system.

Said method can involve the transparent prism having three sides, a first and second of which are offset from one another by said apex angle is modified such that the apex angle is cut away therefrom thereby providing a fourth side which is typically, but not necessarily, substantially parallel to said side of said transparent prism which was opposite said cut away apex angle.

Said method can involve the transparent prism which is modified by removal of said apex angle to provide said fourth side, is hollow and inside of which there is caused to be present a fluid.

Said method can involve the electromagnetic beam being polarized to comprise a "p" component, and it is the selectively the "p" component that is analyzed in step g.

Said method can further comprise:

f) providing a substrate;

g) depositing an anisotropic absorbing thin film on said substrate which is functionally the same as that in step c);

h) causing an incident beam of electromagnetic radiation to reflect from said anisotropic absorbing thin film;

i) applying a detector of said electromagnetic radiation placed at a position such that said beam of electromagnetic radiation that reflects from said anisotropic absorbing thin film enters thereinto;

j) analyzing data produced by said detector to determine optical properties of said anisotropic absorbing thin film; and k) comparing said analyzed data in step j) to that obtained in step e) and evaluating the enhanced sensitivity to surface normal optical functions of anisotropic films achieved by using attenuated total reflection achieved in step g.

Another method to enhance sensitivity to surface-normal optical functions of anisotropic films using attenuated total reflection comprising the steps of:
in either order, steps a) and b):

a) providing a flat transparent substrate having two sides separated by a substrate thickness, said two sides being substantially parallel to one another;

b) providing a transparent prism having three sides, a first and second of which are offset from one another by an apex angle, but from which the apex angle has been removed thereby providing a fourth side that is typically, but not necessarily, substantially parallel to the third side that was opposite the removed apex angle, and wherein said apex angle is sufficient to cause total reflection of an electromagnetic beam entered into the first side of the transparent prism, at the third side of the transparent prism when the ambient is air;

c) depositing an anisotropic absorbing thin film on one of said two sides of said substrate, said anisotropic absorbing thin film having two sides;

d) forming a system by positioning the third side of said transparent prism, on the side of said transparent substrate opposite to that upon which was deposited an anisotropic absorbing thin film.

Said method continues with:

e) causing an incident beam of electromagnetic radiation to enter a first of said two sides of said sensitivity enhancing system that are offset from one another by said apex angle, along a locus that causes it to enter said first side, such that said beam passes through said transparent prism and said transparent substrate, totally internally reflects from both sides of said anisotropic absorbing thin film, passes back through said transparent substrate and transparent prism and exists the second side thereof;

f) causing said electromagnetic radiation to enter a detector of electromagnetic radiation which is positioned such that said beam of electromagnetic radiation that reflected from said thin film and existed said second side of said prism enters thereinto;

g) analyzing data produced by said detector to determine surface-normal optical properties of said anisotropic absorbing thin film with increased sensitivity, as compared to results achievable by direct investigation thereof.

Said method is characterized in that no waveguide effects are required for it to achieve its results, and in that no materials are added to the system formed in steps a)-d) during practice thereof that serve to change reflectivity in said system.

Said method can involve that a refractive index matching material is placed at the point of contact between said transparent substrate and said third side to minimize reflections from said point of contact therebetween, and said material can be a fluid.

Said method can involve said transparent substrate and said transparent prism from which is removed the apex angle are physically merged into one another such that said transparent substrate is a part of said transparent sensitivity enhancement system, and the anisotropic absorbing thin film is directly deposited onto the third side thereof.

Said method can involve the transparent prism which is modified by removal of said apex angle to provide said fourth side, is hollow and inside of which there is caused to be present a fluid.

Said method can involve the electromagnetic beam being polarized to comprise a "p" component, and it is selectively the "p" component that is analyzed.

Said method can further comprise:

h) providing a system which for supporting a sample;

i) depositing an anisotropic absorbing thin film on said system which is functionally the same as that in step c);

j) causing an incident beam of electromagnetic radiation to reflect from said anisotropic absorbing thin film;

k) applying a detector of said electromagnetic radiation placed at a position such that said beam of electromagnetic radiation that reflects from said anisotropic absorbing thin film enters thereinto;

l) analyzing data produced by said detector to determine optical properties of said anisotropic absorbing thin film; and m) comparing said analyzed data in step l) to that obtained in step g) and evaluating the enhanced sensitivity to surface normal optical functions of anisotropic films achieved by using attenuated total reflection achieved in step g.

Another method to enhance sensitivity to surface-normal optical functions of anisotropic films using attenuated total reflection comprising the steps of:

a) providing a transparent prism having three sides, a first and second of which are offset from one another by an apex angle, but which is modified such that the apex angle is cut away therefrom thereby providing a fourth side which is typically, but not necessarily, substantially parallel to said third side of said transparent prism which would be opposite said cut away apex angle were it not removed, and wherein the apex angle is sufficient to cause total reflection of an electromagnetic beam entered into the first side of the transparent prism, at the third side of the transparent prism when the ambient is air;

b) forming a system by depositing an anisotropic absorbing thin film on the third side of said sensitivity enhancing system, said anisotropic absorbing thin film having two sides.

Said method continues with:

c) causing an incident beam of electromagnetic radiation to enter the first of said two sides of said transparent prism that are offset from one another by said apex angle along a locus such that said beam passes through said sensitivity enhancing system, totally internally reflects from both sides of said anisotropic absorbing thin film, passes back through said sensitivity enhancing system and exists the second side thereof;

d) applying a detector of said electromagnetic radiation placed at a position such that said beam of electromagnetic radiation that exists said second side of said sensitivity enhancing system;

e) analyzing data produced by said detector to determine surface-normal optical properties of said anisotropic absorbing thin film with increased sensitivity, as compared to results achievable by direct investigation thereof.

Said method is characterized in that no waveguide effects are required for it to achieve its results, and in that no materials are added to the system after formed in steps a)-b) during practice thereof that serve to change reflectivity in said system.

Said method can involve the transparent prism which is modified by removal of said apex angle to provide said fourth side, is hollow and inside of which there is caused to be present a fluid.

Said method can involve the electromagnetic beam being polarized to comprise a "p" component, and it is the selectively the "p" component that is analyzed in step g.

Said methodology can involve the transparent prism being hollow and there is a liquid present therewithin.

Said method can further comprise:

f) providing a substrate;

g) depositing an anisotropic absorbing thin film on said substrate which is functionally the same as that in step b);

h) causing an incident beam of electromagnetic radiation to reflect from said anisotropic absorbing thin film;

i) applying a detector of said electromagnetic radiation placed at a position such that said beam of electromagnetic radiation that reflects from said anisotropic absorbing thin film enters thereinto;

j) analyzing data produced by said detector to determine optical properties of said anisotropic absorbing thin film; and k) comparing said analyzed data in step j) to that obtained in step e) and evaluating the enhanced sensitivity to surface normal optical functions of anisotropic films achieved by using attenuated total reflection achieved in step e).

The present method works best when the electromagnetic beam is polarized to comprise a "p" component, and it is the selectively the "p" component that is analyzed in step g. This is in contrast to the preference for "s" polarization in the Fujimaki et al. 896 and 024 references.

Said methodology can involve the electromagnetic beam being directed at the first side of the transparent prism at any angle between 0.0 and 90 degrees that causes that angle internally incident on the third face to be greater than the critical angle $$\sin(\text{critical angle}) > n(\text{air})/n(\text{prism}).$$

It is noted that Claims herein include steps that provide that results achieved by investigating an absorbing thin film by use of a FIG. 5a system, (see Detailed Description Section of this Specification), are compared to results achieved by directly investigating a functionally equivalent absorbing thin film investigated by a FIG. 5d system. This additional series of steps is included to overcome any criticism to the end that the results achieved by use of a FIG. 5a system are a result that was simply noticed, but always existed. Making comparison to results achieved by use of a FIG. 5a system to results achieved by use of a FIG. 5d system, is not previously known and no known prior art suggests such.

Finally, for emphasis, it is noted that the present invention does not require any waveguide effects to achieve it's results. It is noted that the invention in Published Patent Applications to Fujimaki et al., Nos. 2013/0293896 and 2014/0170024 does so require combined Surface Plasmon Resonance and Waveguide effects to achieve it's results, as applied to isotropic samples. Further, it is emphasized that during practice of the present invention system no materials are added thereto after it is assembled, which serve to change reflectivity in said system when an electromagnetic beam is applied to investigate the thin film intended to be characterized. Directly stated, the present invention makes no use of waveguide effects, nor does it serve to investigate changes in a thin film sample after the sample is fabricted, as recited in the Claims. The present invention involves using benefits provided by total internal reflection in a FIG. 5a prism-type system, and thus is further not dependent on a requirement that it involve effects based on surface plasmon resonance.

The present invention will be better understood by reference to the Detailed Description Section of this Specification, in conjunction with the Drawings.

BRIEF DESCRIPTION OF THE DRAWINGS

FIGS. 5g' and 5h' show graphical presentations of Electric Field Magnitude in the samples of FIGS. 5g and 5h.

DETAILED DESCRIPTION

Figure 1:
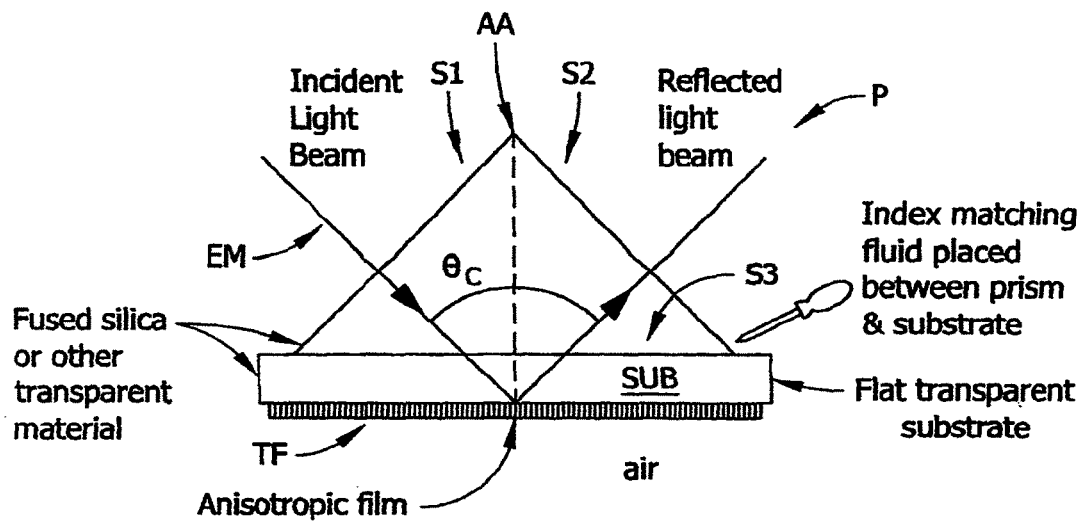
FIGS. 1 and 2 show a transparent prism having three sides, and a separate substrate upon one side thereof is deposited a thin film.
Figure 2:
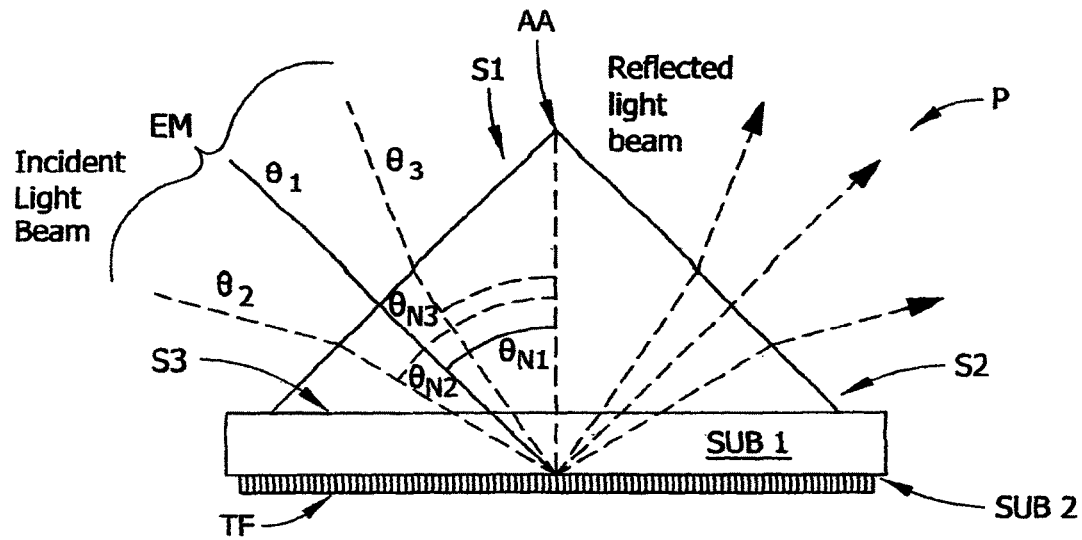

Turning now to the Drawings, FIGS. 1 and 2 show a transparent prism (P) having three sides, a first (S1) and second (S2) of which are offset from one another by an apex angle (AA) which is sufficient to cause total reflection of an electromagnetic beam entered into the first side (S1) of the transparent prism (P), at the third side (S3) of the transparent prism when the ambient is air, and a transparent substrate (SUB) having first and second substantially parallel sides separated by a substrate thickness. Note that an anisotropic absorbing thin film (TF) is deposited on one side (SBU2) of said substrate (SUB), and that said third side (S3) of said prism (P), which is opposite the apex angle (AA), is in contact with the side (SUB1) of the substrate (SUB) opposite that onto which was deposited the anisotropic absorbing thin film (TF).

Figure 3:
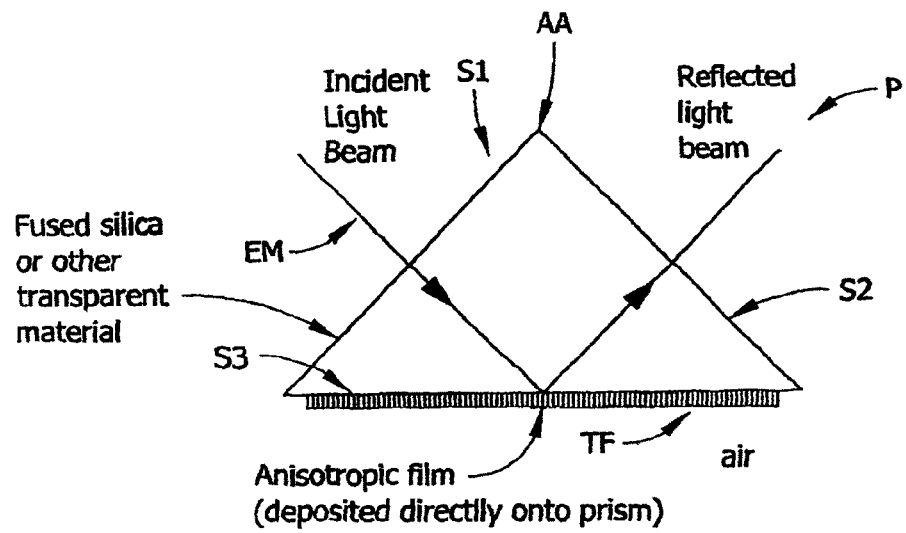
FIG. 3 shows a system similar to that in FIGS. 1 and 2, but indicates that the prism and substrate have been effectively merged into one another.

FIG. 3 shows a system similar to that in FIGS. 1 and 2, but indicates that the prism (P) and substrate (SUB) have been effectively merged into one another, in that the anisotropic thin film (TF) is deposited directly on the third side (S3) of the prism (P).

Figure 4:
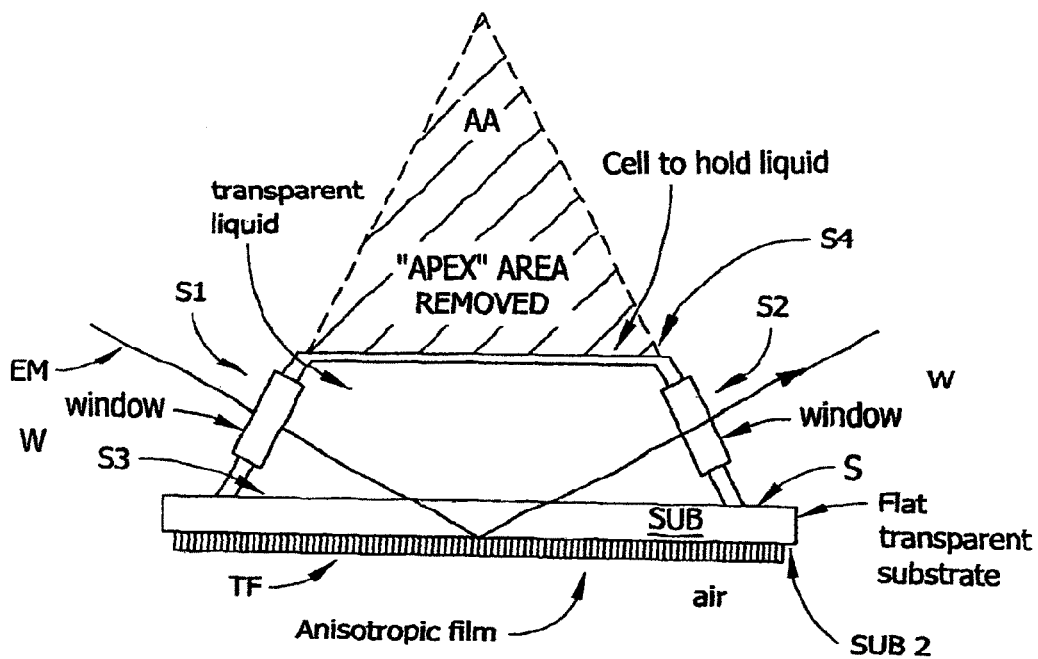
FIG. 4 shows a sensitivity enhancement system comprising a three sided prism, a first and second of which sides are offset from one another by an apex angle, but from which the apex angle has been removed.

FIG. 4 shows a sensitivity enhancement system comprising what can be described as a transparent prism having three sides, a first (S1) and second of which are offset from one another by an apex angle (AA), but from which the apex angle (AA) has been removed thereby providing a fourth side (S4) that is typically, but not necessarily, substantially parallel to the third side (S3) that was opposite the removed apex angle (AA), and wherein said apex angle (AA) is sufficient to cause total reflection of an electromagnetic beam (EM) entered into the first side (S1) of the transparent prism (P), at the third side (S3) of the transparent prism (P) when the ambient is air. Note that electromagnetic radiation transparent "windows" (W) are also indicated, but are not required where the prism material is transparent thereto.

Again, the sensitivity enhancing system can be separate from a substrate and set atop a substrate on a side thereof opposite to that upon which is deposited a thin film, or the anisotropic thin film can be directly deposited onto the third side thereof which is opposite the removed apex angle region.

Figure 5A:
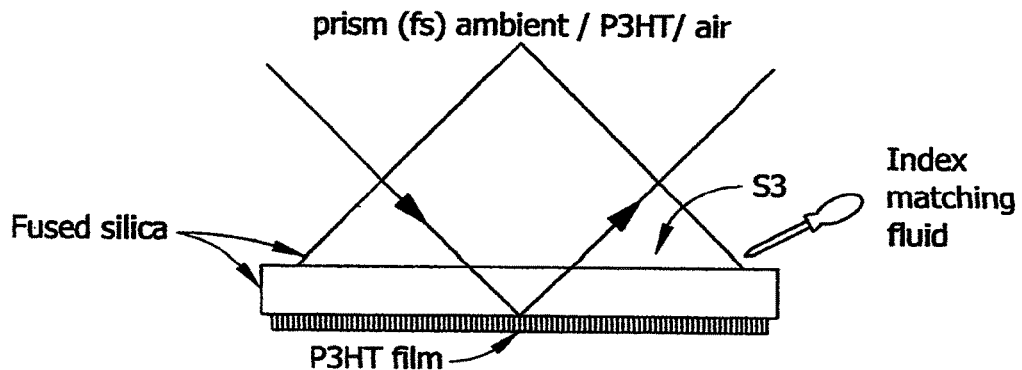
FIG. 5a shows a transparent Prism applied to acquire the data in FIGS. 5b and 5c.
Figure 5B:
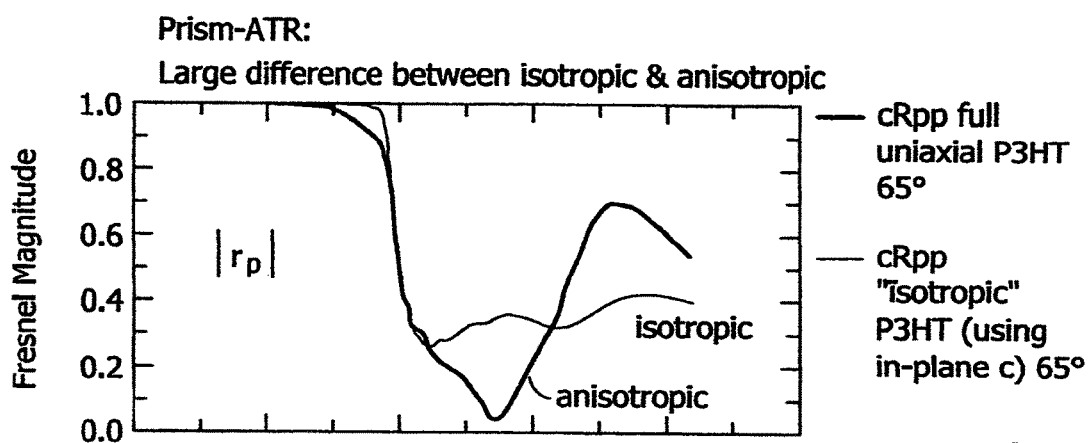
FIGS. 5b and 5c show Fresnel Magnitudes and Psi Degrees, respectively, for isotropic and anisotropic data collected using the system of FIG. 5a, as a function of photon energy.
Figure 5C:
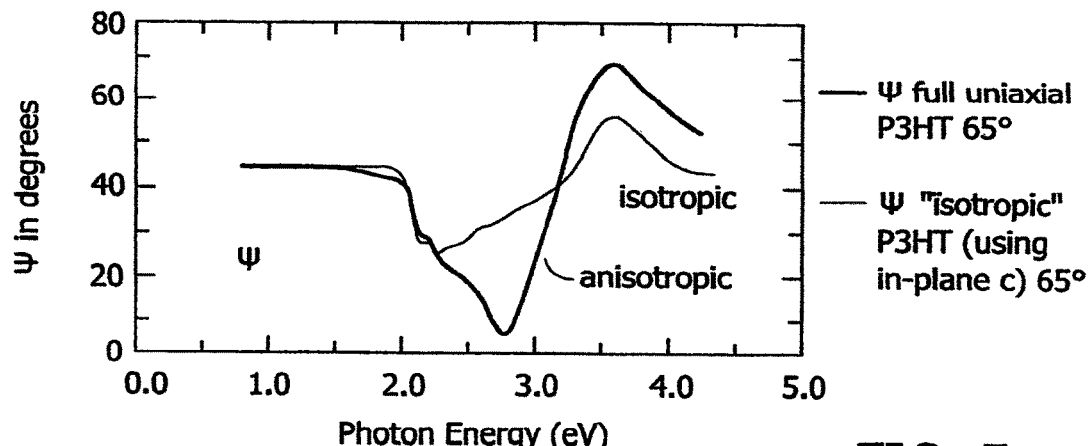

FIG. 5a shows a transparent Prism applied to acquire the data in FIGS. 5b and 5c. FIGS. 5b and 5c show Fresnel Magnitudes and Psi Degrees, respectively, for isotropic and anisotropic data collected using the system of FIG. 5a.

Figure 5D:
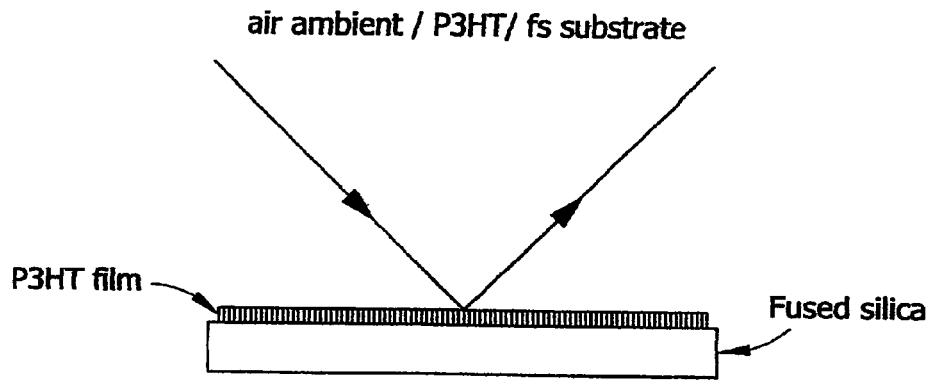
FIG. 5d shows a system used to acquire data presented in FIGS. 5e and 5f.
Figure 5E:
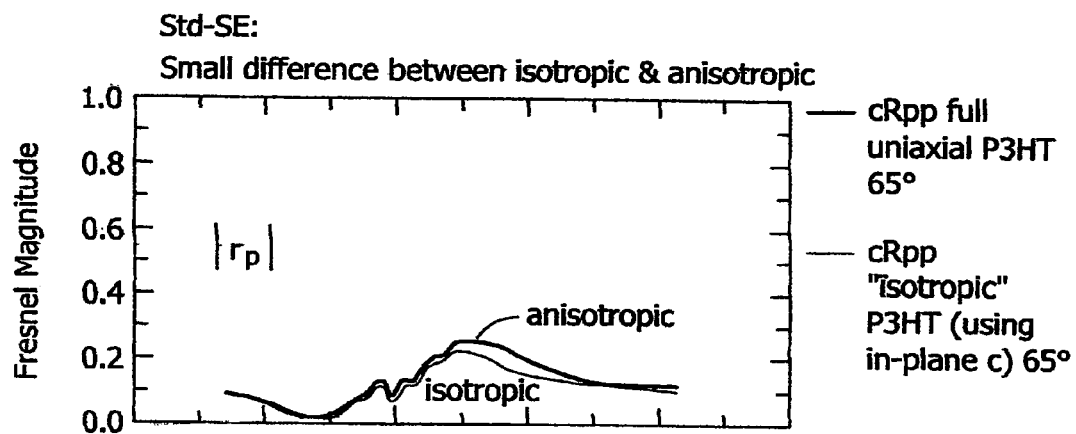
FIGS. 5e and 5f show Fresnel Magnitudes and Psi Degrees, respectively, for isotropic and anisotropic data collected using the system of FIG. 5d, as a function of photon energy.
Figure 5F:
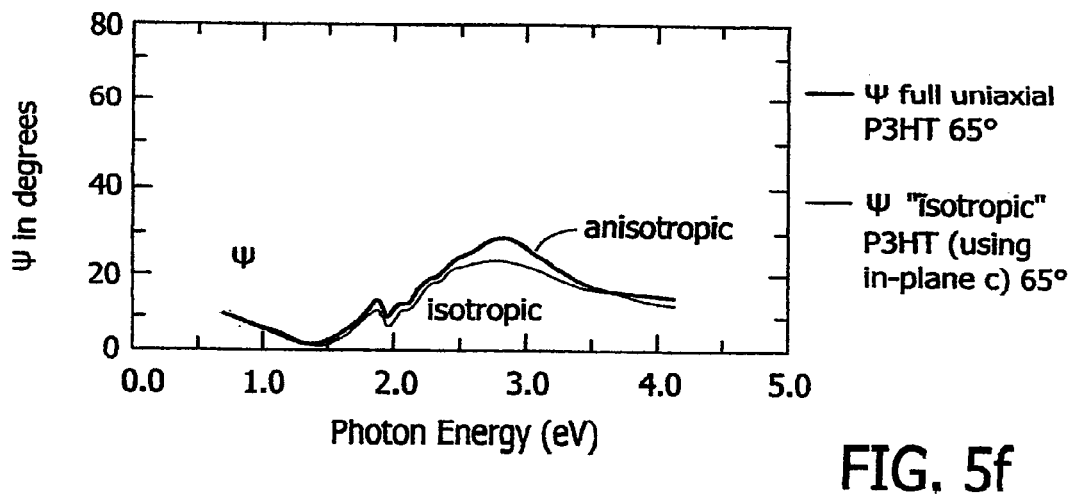

FIG. 5d shows a system used to acquire data presented in FIGS. 5e and 5f. FIGS. 5e and 5f show Fresnel Magnitudes and Psi Degrees, respectively, for reflected isotropic and anisotropic data collected using the system of FIG. 5a.

Figure 5G:
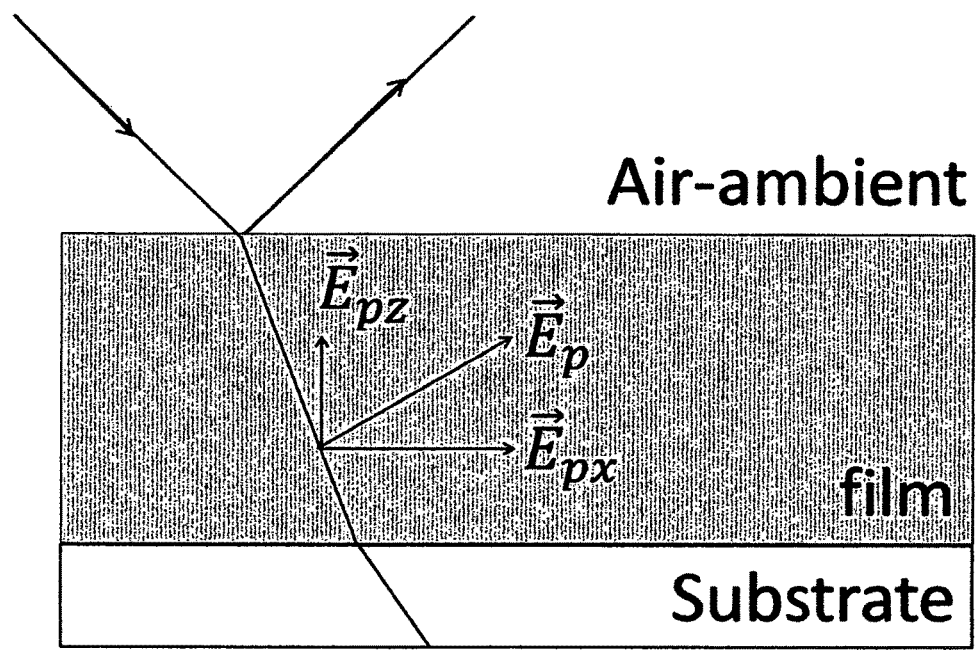
FIGS. 5g and 5h show demonstrative "P" direction Polarization in the settings of FIGS. 5d and 5a respectively.

The focus of the present invention is appreciated by comparing the data in FIGS. 5b and 5c with that in FIGS. 5e and 5f. Note in particular that the anisotropic data shown in FIGS. 5b and 5c is much more pronounced than is that shown in FIGS. 5e and 5f. This is because electric fields are affected differently by the systems of FIGS. 5a and 5d. When using the configuration of FIG. 5d, only a small portion of the incident P-polarized electric field is oriented normal to the surface, but when using the configuration of FIG. 5a, total internal reflection occurs and a significantly larger portion of the P-polarized incident electric field is oriented toward the surface, as compared to the result when FIG. 5d is used, (which is a more typical measurement mode with an air ambient). FIGS. 5g' and 5h' show this.

Figure 5H:
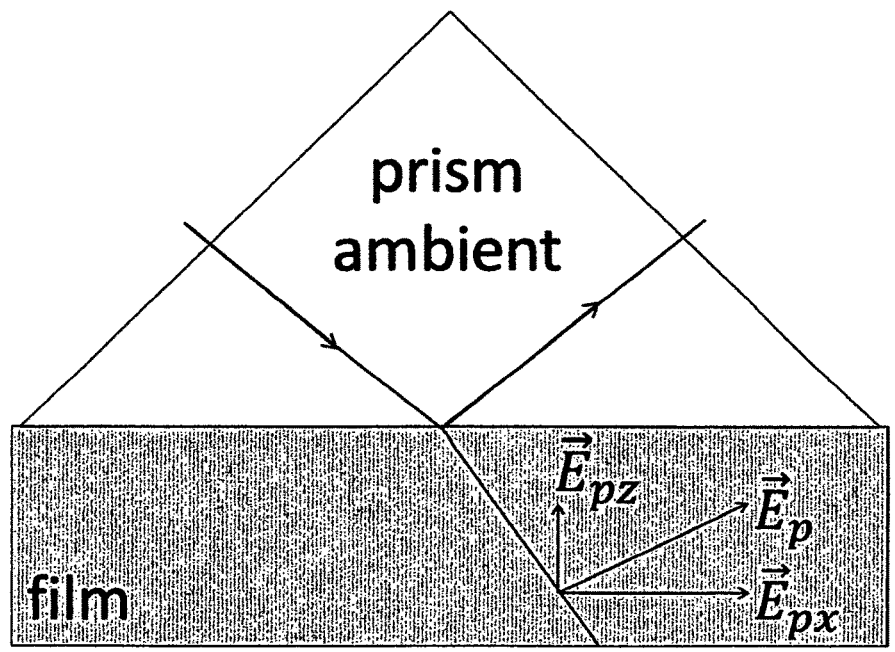
Figure 5G:
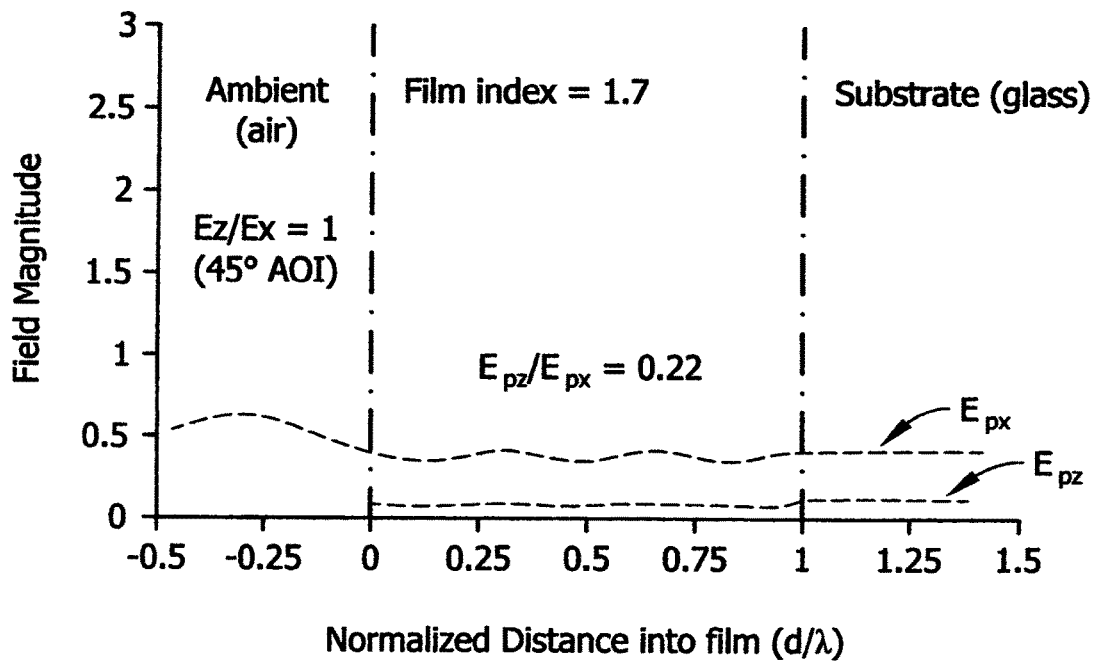
Figure 5H:
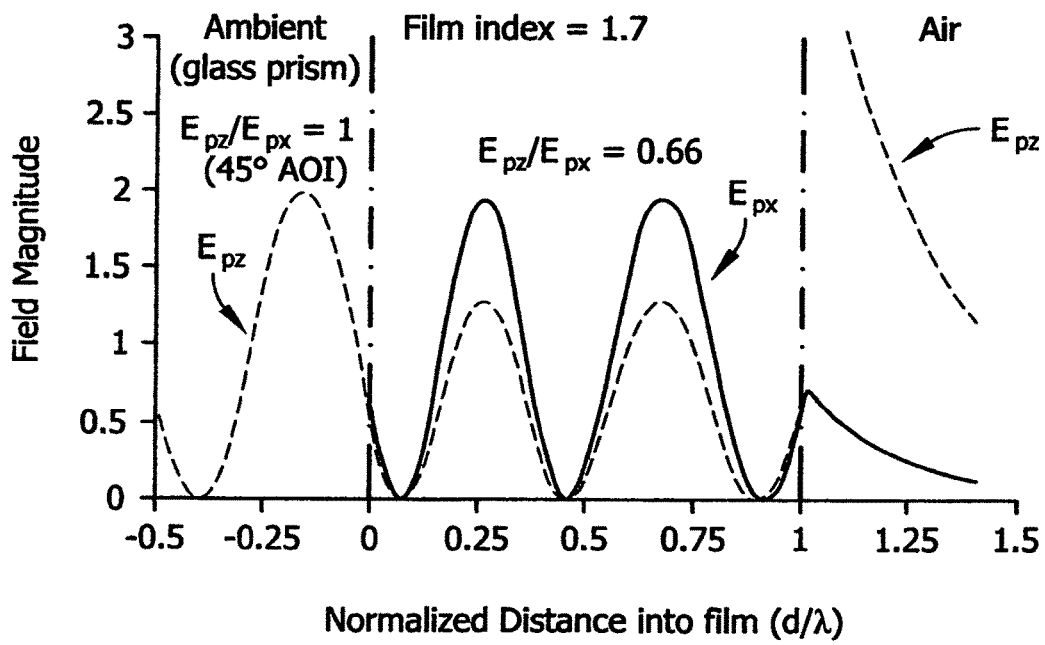

FIGS. 5g and 5h show demonstrative "P" direction Polarization in the settings of FIGS. 5d and 5a respectively. FIGS. 5g' and 5h' show graphical presentations of Electric Field Magnitude in the thin films of FIGS. 5g and 5h. In both cases the thin films are investigated by an oblique angle of incidence beam of electromagnetic radiation. Note that in the total internal reflection configuration of FIG. 5h, a significantly larger portion of the P-polarized electric field is oriented normal to the surface, (see Epz in FIG. 5h') as compared to the scenario in FIG. 5g, wherein a significantly smaller portion of the P-polarized component of the electric field, (Epz in FIG. 5g'), is oriented normal to the film surface in an anisotropic film.

Figure 6A:
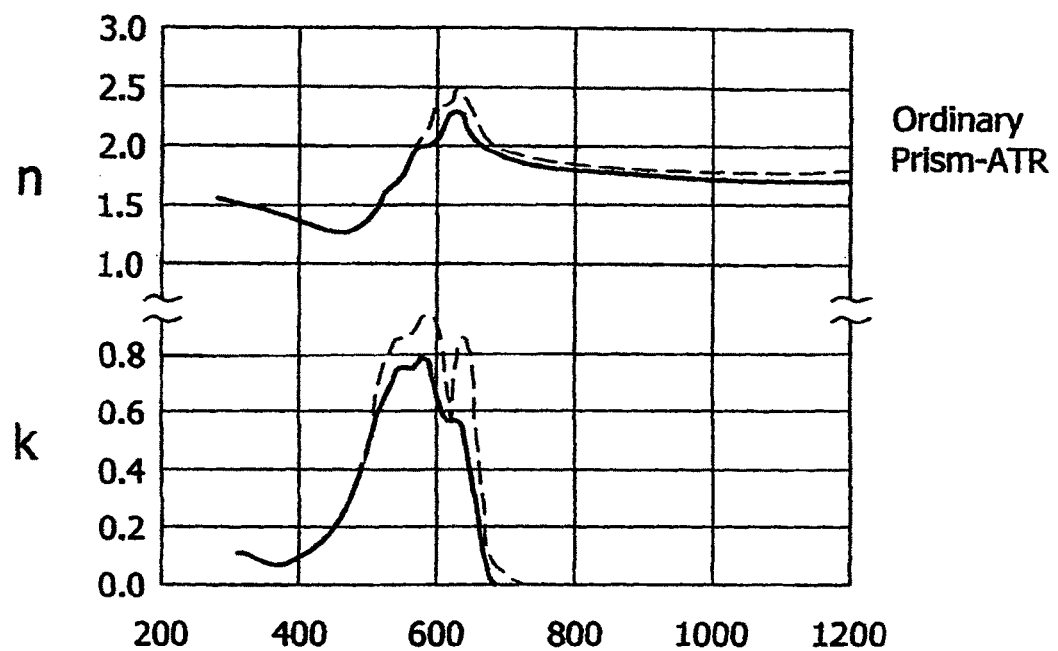
FIGS. 6a and 6b show Refractive Index and Extinction Coefficient for Ordinary and Extraordinary Prism-ATR data as a function of wavelength.
Figure 6B:
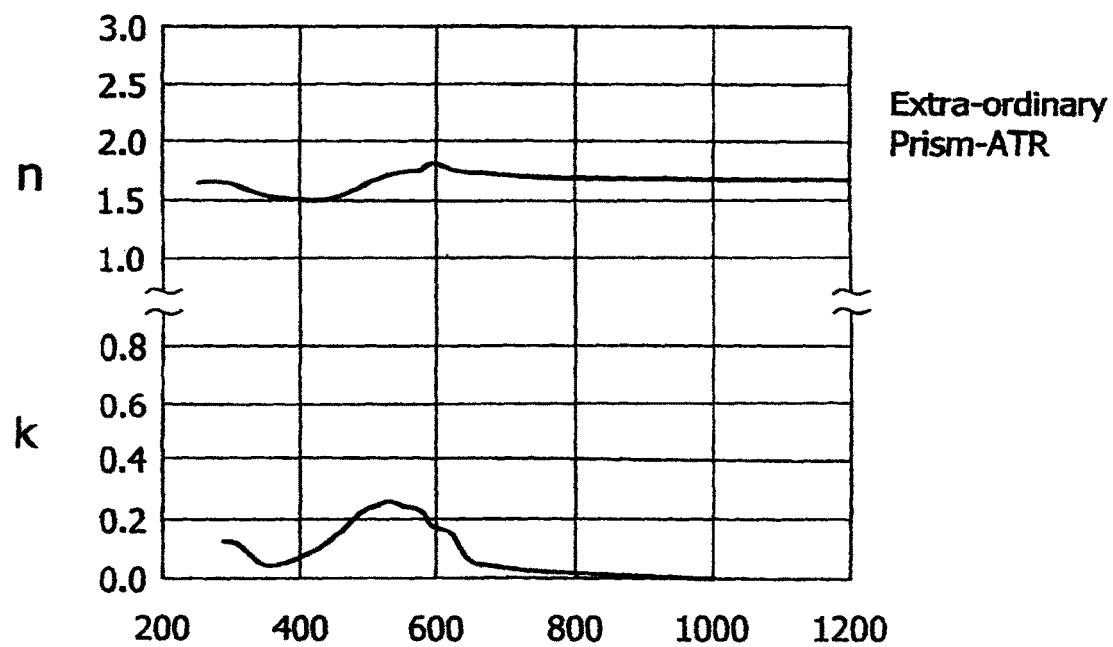

FIGS. 6a and 6b show Refractive Index and Extinction Coefficient for Ordinary and Extraordinary Prism-ATR data.

For clarity, it is noted that the term "absorbing" as used with respect to thin films, refers to a thin film that is not completely transparent to electromagnetic radiation. That is, the wavelength is sufficiently short so that its energy is high enough to excite atoms therewithin that are encountered.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method to enhance sensitivity to surface-normal optical functions of anisotropic absorbing thin films using attenuated total reflection comprising the steps of: in either order, steps a) and b):

a) providing a transparent prism having three sides, a first and second of which are offset from one another by an apex angle which is sufficient to cause total reflection of an electromagnetic beam entered into the first side of the transparent prism, at the third side of the transparent prism when the ambient is air;

b) providing a transparent substrate having first and second substantially parallel sides separated by a substrate thickness;

c) depositing an anisotropic absorbing thin film on one side of said substrate, said anisotropic absorbing thin film having two sides;

d) forming a system by positioning said third side of said prism which is opposite the apex angle, in contact with the side of the substrate opposite that onto which was deposited the anisotropic absorbing thin film;

e) causing an incident beam of electromagnetic radiation to enter the first of said two sides of said transparent prism that are offset from one another by said apex angle along a locus such that said beam passes through said transparent prism and transparent substrate, totally internally reflects from both sides of said anisotropic absorbing thin film, passes back through said transparent substrate and transparent prism and exists the second side thereof;

f) applying a detector of said electromagnetic radiation placed at a position such that said beam of electromagnetic radiation that exists said second side of said prism enters thereinto;

g) analyzing data produced by said detector to determine surface-normal optical properties of said anisotropic absorbing thin film with increased sensitivity, as compared to results achievable by direct investigation thereof;

said method being characterized in that no waveguide effects are required for it to achieve its results, and in that no materials are added to the system formed in steps a)-d) during use that serve to change reflectivity in said system.

2. A method as in claim 1 in which refractive index matching material is placed at the point of contact between said transparent substrate and said transparent prism to minimize reflections from said point of contact therebetween.

3. A method as in claim 2 in which said refractive index matching material is a fluid.

4. A method as in claim 1 in which the transparent prism and transparent substrate are merged into a single element and the anisotropic absorbing thin film is deposited onto the third side of the transparent prism that is opposite the apex degree angle.

5. A method as in claim 1 in which the transparent prism having three sides, a first and second of which are offset from one another by said apex is modified such that the apex angle is cut away therefrom thereby providing a fourth side which is typically, but not necessarily, substantially parallel to said side of said transparent prism which was opposite said cut away apex angle which is positioned on the side of said transparent substrate opposite to that upon which was deposited a anisotropic absorbing thin film.

6. A method as in claim 4 in which the transparent prism which is modified by removal of said apex angle to provide said fourth side, is hollow and inside of which there is caused to be present a fluid.

7. A method as in claim 1 in which the electromagnetic beam is polarized to comprise a "p" component, and it is the selectively the "p" component that is analyzed in step g.

8. A method to enhance sensitivity to surface-normal optical functions of anisotropic films using attenuated total reflection comprising the steps of:
   a) providing a transparent prism having three sides, a first and second of which are offset from one another by an apex angle which is sufficient to cause total reflection of an electromagnetic beam entered into the first side of the transparent prism, at the third side of the transparent prism when the ambient is air;
   b) forming a system by depositing an anisotropic absorbing thin film on the third side of said prism which is opposite said apex angle, said anisotropic absorbing thin film having two sides;
   c) causing an incident beam of electromagnetic radiation to enter the first of said two sides of said transparent prism that are offset from one another by said apex angle, along a locus such that said beam passes through said transparent prism, totally internally reflects from both sides of said anisotropic absorbing thin film, passes back through said transparent prism and exists the second side thereof;
   d) applying a detector of said electromagnetic radiation placed at a position such that said beam of electromagnetic radiation that exists said second side of said prism enters thereinto;
   e) analyzing data produced by said detector to determine surface-normal optical properties of said anisotropic absorbing thin film with increased sensitivity, as compared to results achievable by direct investigation thereof;
said method being characterized in that no waveguide effects are required for it to achieve its results, and in that no materials are added to the system formed in steps a)-b) during practice thereof that serve to change reflectivity in said system.

9. A method as in claim 8 in which the transparent prism having three sides, a first and second of which are offset from one another by said apex angle is modified such that the apex angle is cut away therefrom thereby providing a fourth side which is typically, but not necessarily, substantially parallel to said side of said transparent prism which was opposite said cut away apex angle.

10. A method as in claim 9 in which the transparent prism which is modified by removal of said apex angle to provide said fourth side, is hollow and inside of which there is caused to be present a fluid.

11. A method as in claim 8 in which the electromagnetic beam is polarized to comprise a "p" component, and it is the selectively the "p" component that is analyzed in step g.

12. A method to enhance sensitivity to surface-normal optical functions of anisotropic films using attenuated total reflection comprising the steps of:
   in either order, steps a) and b):
   a) providing a flat transparent substrate having two sides separated by a substrate thickness, said two sides being substantially parallel to one another;
   b) providing a transparent prism having three sides, a first and second of which are offset from one another by an apex angle, but from which the apex angle has been removed thereby providing a fourth side that is typically, but not necessarily, substantially parallel to the third side that was opposite the removed apex angle, and wherein said apex angle is sufficient to cause total reflection of an electromagnetic beam entered into the first side of the transparent prism, at the third side of the transparent prism when the ambient is air;
   c) depositing an anisotropic absorbing thin film on one of said two sides of said substrate, said anisotropic absorbing thin film having two sides;
   d) forming a system by positioning the third side of said transparent prism, on the side of said transparent substrate opposite to that upon which was deposited an anisotropic absorbing thin film;
   e) causing an incident beam of electromagnetic radiation to enter a first of said two sides of said transparent prism that are offset from one another by said apex angle, along a locus that causes it to enter said first side, such that said beam passes through said transparent prism and said transparent substrate, totally internally reflects from both sides of said anisotropic absorbing thin film, passes back through said transparent substrate and transparent prism and exists the second side thereof;
   f) causing said electromagnetic radiation to enter a detector of electromagnetic radiation which is positioned such that said beam of electromagnetic radiation that reflected from said thin film and existed said second side of said prism enters thereinto;
   g) analyzing data produced by said detector to determine surface-normal optical properties of said anisotropic absorbing thin film with increased sensitivity, as compared to results achievable by direct investigation thereof;
said method being characterized in that no waveguide effects are required for it to achieve its results, and in that no materials are added to the system formed in steps a)-d) during practice thereof that serve to change reflectivity in said system.

13. A method as in claim 12 in which refractive index matching material is placed at the point of contact between said transparent substrate and said third side to minimize reflections from said point of contact therebetween.

14. A method as in claim 13 in which said refractive index matching material is a fluid.

15. A method as in claim 12 in which said transparent substrate and said transparent prism from which is removed the apex angle are physically merged into one another such that said transparent substrate is a part of said transparent prism, and the anisotropic absorbing thin film is directly deposited onto the third side thereof.

16. A method as in claim 12 in which the transparent prism which is modified by removal of said apex angle to provide said fourth side, is hollow and inside of which there is caused to be present a fluid.

17. A method as in claim 12 in which the electromagnetic beam is polarized to comprise a "p" component, and it is selectively the "p" component that is analyzed.

18. A method to enhance sensitivity to surface-normal optical functions of anisotropic films using attenuated total reflection comprising the steps of:
   a) providing a transparent prism having three sides, a first and second of which are offset from one another by an apex angle, but which is modified such that the apex angle is cut away therefrom thereby providing a fourth side which is typically, but not necessarily, substantially parallel to said third side of said transparent prism which would be opposite said cut away apex angle were it not removed, and wherein the apex angle is sufficient to cause total reflection of an electromagnetic beam entered into the first side of the transparent prism, at the third side of the transparent prism when the ambient is air;

b) forming a system by depositing an anisotropic absorbing thin film on the third side of said transparent prism, said anisotropic absorbing thin film having two sides;

c) causing an incident beam of electromagnetic radiation to enter the first of said two sides of said transparent prism that are offset from one another by said apex angle along a locus such that said beam passes through said sensitivity enhancing system, totally internally reflects from both sides of said anisotropic absorbing thin film, passes back through said transparent prism and exists the second side thereof;

d) applying a detector of said electromagnetic radiation placed at a position such that said beam of electromagnetic radiation that exists said second side of said sensitivity enhancing system;

e) analyzing data produced by said detector to determine surface-normal optical properties of said anisotropic absorbing thin film with increased sensitivity, as compared to results achievable by direct investigation thereof;

said method being characterized in that no waveguide effects are required for it to achieve its results, and in that no materials are added to the system formed in steps a)-b) during practice thereof that serve to change reflectivity in said system.

19. A method as in claim 18 in which the transparent prism which is modified by removal of said apex angle to provide said fourth side, is hollow and inside of which there is caused to be present a fluid.

20. A method as in claim 18 in which the electromagnetic beam is polarized to comprise a "p" component, and it is the selectively the "p" component that is analyzed in step g.

21. A method as in claim 1, wherein the electromagnetic beam is directed at he first side of the transparent prism at any angle between 0.0 and 90 degrees that causes that angle internally incident on the third face to be greater than the critical angle $$\sin(\text{critical angle}) > n(\text{air})/n(\text{prism}).$$

22. A method as in claim 8, wherein the electromagnetic beam is directed at he first side of the transparent prism at any angle between 0.0 and 90 degrees that causes that angle internally incident on the third face to be greater than the critical angle $$\sin(\text{critical angle}) > n(\text{air})/n(\text{prism}).$$

23. A method as in claim 12, wherein the electromagnetic beam is directed at he first side of the transparent prism at any angle between 0.0 and 90 degrees that causes that angle internally incident on the third face to be greater than the critical angle $$\sin(\text{critical angle}) > n(\text{air})/n(\text{prism}).$$

24. A method as in claim 18, wherein the electromagnetic beam is directed at he first side of the transparent prism at any angle between 0.0 and 90 degrees that causes that angle internally incident on the third face to be greater than the critical angle $$\sin(\text{critical angle}) > n(\text{air})/n(\text{prism}).$$

25. A method as in claim 1 where the transparent prism is hollow and there is a liquid present therewithin.

26. A method as in claim 8 where the transparent prism is hollow and there is a liquid present therewithin.

27. A method as in claim 1, which further comprises:

h) providing a substrate;

i) depositing an anisotropic absorbing thin film on said substrate which is functionally the same as that in step c);

j) causing an incident beam of electromagnetic radiation to reflect from said anisotropic absorbing thin film;

k) applying a detector of said electromagnetic radiation placed at a position such that said beam of electromagnetic radiation that reflects from said anisotropic absorbing thin film enters thereinto;

l) analyzing data produced by said detector to determine optical properties of said anisotropic absorbing thin film; and m) comparing said analyzed data in step l) to that obtained in step g) and evaluating the enhanced sensitivity to surface normal optical functions of anisotropic films achieved by using attenuated total reflection achieved in step g.

28. A method as in claim 8, which further comprises:

f) providing a substrate for supporting a sample;

g) depositing an anisotropic absorbing thin film on said substrate which is functionally the same as that in step b);

h) causing an incident beam of electromagnetic radiation to reflect from said anisotropic absorbing thin film;

i) applying a detector of said electromagnetic radiation placed at a position such that said beam of electromagnetic radiation that reflects from said anisotropic absorbing thin film enters thereinto;

j) analyzing data produced by said detector to determine optical properties of said anisotropic absorbing thin film; and k) comparing said analyzed data in step j) to that obtained in step e) and evaluating the enhanced sensitivity to surface normal optical functions of anisotropic films achieved by using attenuated total reflection achieved in step e).

29. A method as in claim 12, which further comprises:

h) providing a substrate;

i) depositing an anisotropic absorbing thin film on said substrate which is functionally the same as that in step b);

j) causing an incident beam of electromagnetic radiation to reflect from said anisotropic absorbing thin film;

k) applying a detector of said electromagnetic radiation placed at a position such that said beam of electromagnetic radiation that reflects from said anisotropic absorbing thin film enters thereinto;

l) analyzing data produced by said detector to determine optical properties of said anisotropic absorbing thin film; and m) comparing said analyzed data in step l) to that obtained in step g) and evaluating the enhanced sensitivity to surface normal optical functions of anisotropic films achieved by using attenuated total reflection achieved in step g.

30. A method as in claim 18, which further comprises:

f) providing a substrate;

g) depositing an anisotropic absorbing thin film on said substrate which is functionally the same as that in step b);

h) causing an incident beam of electromagnetic radiation to reflect from said anisotropic absorbing thin film;

i) applying a detector of said electromagnetic radiation placed at a position such that said beam of electromagnetic radiation that reflects from said anisotropic absorbing thin film enters thereinto;

j) analyzing data produced by said detector to determine optical properties of said anisotropic absorbing thin film; and k) comparing said analyzed data in step j) to that obtained in step e) and evaluating the enhanced sensitivity to surface normal optical functions of anisotropic films achieved by using attenuated total reflection achieved in step e).

\* \* \* \* \*